United States Patent
Suriye et al.

(10) Patent No.: US 10,350,587 B2
(45) Date of Patent: Jul. 16, 2019

(54) CATALYST SYSTEM FOR OLEFIN METATHESIS

(71) Applicant: TERRAMARK MARKENCREATION GMBH

(72) Inventors: Kongkiat Suriye, Samutprakan (TH); Burin Khemthong, Samutprakan (TH)

(73) Assignee: SMH Co., Ltd, Bangkok (TH)

( * ) Notice: Subject to any disclaimer, the term of this patent is extended or adjusted under 35 U.S.C. 154(b) by 0 days.

(21) Appl. No.: 15/515,720

(22) PCT Filed: Mar. 16, 2016

(86) PCT No.: PCT/EP2016/055700
§ 371 (c)(1),
(2) Date: Mar. 30, 2017

(87) PCT Pub. No.: WO2016/150794
PCT Pub. Date: Sep. 29, 2016

(65) Prior Publication Data
US 2017/0297009 A1     Oct. 19, 2017

(30) Foreign Application Priority Data
Mar. 20, 2015 (EP) .................................. 15160033

(51) Int. Cl.
*B01J 35/00* (2006.01)
*B01J 27/232* (2006.01)
(Continued)

(52) U.S. Cl.
CPC ......... *B01J 35/0006* (2013.01); *B01J 23/007* (2013.01); *B01J 23/02* (2013.01); *B01J 27/232* (2013.01); *B01J 27/25* (2013.01); *B01J 29/076* (2013.01); *B01J 29/166* (2013.01); *B01J 29/48* (2013.01); *B01J 29/7038* (2013.01);
(Continued)

(58) Field of Classification Search
CPC ... B01J 23/02; B01J 23/24; B01J 23/32; B01J 23/69; B01J 29/076; B01J 29/48; B01J 29/7038; B01J 29/7815; B01J 29/7876; B01J 35/006; C07C 2523/16
See application file for complete search history.

(56) References Cited

U.S. PATENT DOCUMENTS

| | | |
|---|---|---|
| 3,658,929 A | 4/1972 | Banks |
| 4,522,936 A | 6/1985 | Kukes et al. |

(Continued)

FOREIGN PATENT DOCUMENTS

| | | | | |
|---|---|---|---|---|
| EP | 3050621 A1 | 8/2016 | | |
| WO | WO-2014163590 A1 * | 10/2014 | ............ | B01J 21/10 |

(Continued)

OTHER PUBLICATIONS

International Search Report and Written Opinion—PCT/EP2016/055700—dated Jun. 24, 2016.
(Continued)

*Primary Examiner* — Jun Li
(74) *Attorney, Agent, or Firm* — Banner & Witcoff, Ltd.

(57) ABSTRACT

The present invention relates to a catalyst system for olefin metathesis, the catalyst system comprising: a) a first system zone substantially comprising a layered double hydroxide; and b) a second system zone comprising a metathesis catalyst.

20 Claims, 1 Drawing Sheet

Alternative 1

Alternative 2

Figure 1:
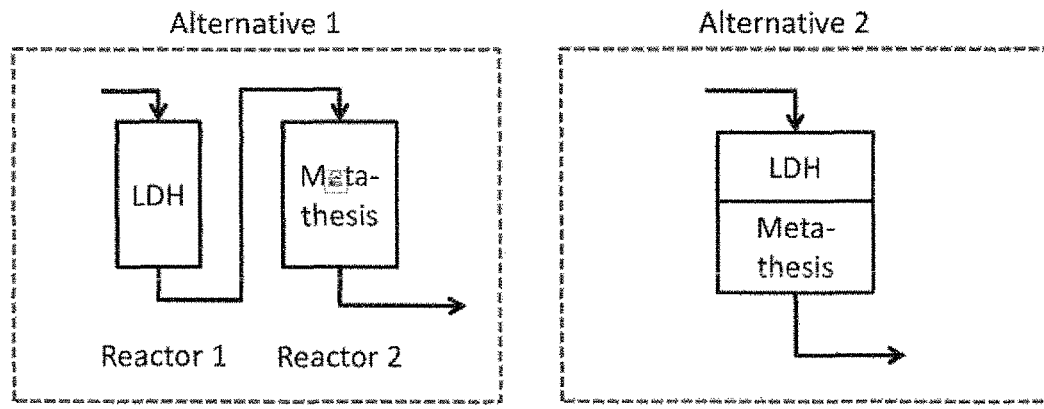

(51) Int. Cl.
| | |
|---|---|
| *B01J 27/25* | (2006.01) |
| *B01J 23/02* | (2006.01) |
| *B01J 29/70* | (2006.01) |
| *B01J 29/78* | (2006.01) |
| *B01J 38/52* | (2006.01) |
| *C07C 6/04* | (2006.01) |
| *B01J 37/04* | (2006.01) |
| *B01J 23/00* | (2006.01) |
| *B01J 29/076* | (2006.01) |
| *B01J 29/16* | (2006.01) |
| *B01J 29/48* | (2006.01) |
| *B01J 35/02* | (2006.01) |
| *B01J 23/24* | (2006.01) |
| *B01J 23/32* | (2006.01) |
| *B01J 29/69* | (2006.01) |

(52) U.S. Cl.
CPC ....... *B01J 29/7815* (2013.01); *B01J 29/7876* (2013.01); *B01J 35/02* (2013.01); *B01J 37/04* (2013.01); *B01J 38/52* (2013.01); *C07C 6/04* (2013.01); *B01J 23/24* (2013.01); *B01J 23/32* (2013.01); *B01J 29/163* (2013.01); *B01J 29/69* (2013.01); *C07C 2521/08* (2013.01); *C07C 2523/16* (2013.01); *C07C 2523/30* (2013.01); *C07C 2529/08* (2013.01); *Y02P 20/52* (2015.11)

(56) References Cited

U.S. PATENT DOCUMENTS

| | | | |
|---|---|---|---|
| 4,575,575 | A | 3/1986 | Drake et al. |
| 5,120,894 | A | 6/1992 | McCauley |
| 5,120,896 | A | 6/1992 | Kemp et al. |
| 2008/0194903 | A1 | 8/2008 | Schubert et al. |
| 2008/0312485 | A1 | 12/2008 | Takai et al. |
| 2010/0145126 | A1 | 6/2010 | Takai et al. |
| 2010/0167911 | A1 | 7/2010 | Shum |
| 2011/0172475 | A1 | 7/2011 | Peters et al. |
| 2011/0288256 | A1* | 11/2011 | Vermeiren ............ C07C 11/08 526/348.6 |
| 2013/0252804 | A1* | 9/2013 | Ramachandran ...... B01J 23/007 502/176 |
| 2014/0179973 | A1* | 6/2014 | Debecker ................ B01J 27/19 585/644 |

FOREIGN PATENT DOCUMENTS

| | | |
|---|---|---|
| WO | 2016/068814 A1 | 5/2016 |
| WO | 2016/120423 A1 | 8/2016 |

OTHER PUBLICATIONS

A. Spamer et al. (Applied Catalysis A: General 255 (2013), p. 133-142).

H. Liu et al. (Journal of Natural Gas Chemistry 18 (2009), p. 331-336).

Banks et al. (Journal of Molecular Catalysis 28 (1-3) (1985) p. 117-131).

* cited by examiner

CATALYST SYSTEM FOR OLEFIN METATHESIS

CROSS-REFERENCE TO RELATED APPLICATIONS

This application is a U.S. National Stage application under 35 U.S.C. § 371 of International Application PCT/EP2016/055700 (published as WO 2016/150794 A1), filed Mar. 16, 2016, which claims the benefit of priority to EP 15160033.5, filed Mar. 20, 2015. Benefit of the filing date of each of these prior applications is hereby claimed. Each of these prior applications is hereby incorporated by reference in its entirety.

TECHNICAL FIELD OF THE INVENTION

The present invention relates to a catalyst system for olefin metathesis and an olefin metathesis process conducted by using the inventive catalyst system.

BACKGROUND OF THE INVENTION

Metathesis is one of a crucial reaction for the petrochemicals industry, especially the cross-metathesis of ethene and n-butene which is an economical mean for selectively producing highly demanded propene. Factors affecting feasibility of the process include conversion, selectivity, energy consumption, and reaction cycle time.

Attempts have been made in improving overall efficiency of olefin metathesis process. Several approaches were employed. For example, U.S. Pat. No. 4,575,575 discloses a metathesis reaction between ethene and 2-butene carrying out in the presence of a catalyst of silica-supported tungsten oxide in combination with a magnesium oxide co-catalyst.

U.S. Pat. No. 3,658,929 discloses processes for olefins conversion, including olefins metathesis, wherein the olefins feeds are pretreated by contacting with magnesium oxide prior to the conversion.

U.S. Pat. No. 5,120,894 also discloses a process for olefin conversion wherein the reaction zone is a catalyst bed configured so that the upstream end of the bed is magnesium oxide and the downstream end of the bed is a mixture of magnesium oxide and tungsten oxide on silica catalyst.

In these disclosures magnesium oxide was used to perform double bond isomerization of the olefin feed, such as isomerization of 1-butene to 2-butene, in order to achieve higher olefin conversion rate. However, magnesium oxide normally sinters at high temperature and therefore its performance usually drops significantly after regeneration.

US 20100145126 A1 discloses a process of producing olefins through a metathesis reaction, wherein the catalytic reactivity is improved by allowing co-existence of hydrogen gas. However, side reactions can occur between hydrogen and olefin feed or product and therefore product yield is reduced.

US 2008/0194903 A1 discloses a method for purifying a starting product comprising contacting a feed stream with an adsorbent which has been activated comprising at least 3% by weight of aluminum oxide to remove one or more impurities from the feed stream. The adsorbent activation is conducted at high temperature and therefore high energy is required.

Another factor that could play an important role on metathesis catalyst efficiency is in the catalyst shaping process. Typically, heterogeneous catalysts, including metathesis catalyst, are initially prepared in powder form. They needed to be shaped into an appropriate structure, for example, sphere, tablet, or extrudate, prior to be used in an industrial process.

An appropriate structure provides good mechanical strength, easier handling, and prevent high process pressure drop. A catalyst binder is usually added to the catalyst composition during catalyst shaping process for binding powder materials together. Choices of binder can significantly affect physical properties and also catalytic performance of the final catalyst. If a proper hinder that does not adversely affect catalyst efficiency can't be identified or obtained, a suitable solution needed to be figured out in order to resume catalyst efficiency during its utilization in the process.

SUMMARY OF THE INVENTION

It is therefore an object of the present invention to provide a catalyst system overcoming drawbacks of the prior art, in particular featuring high productivity and good stability. It is a further object to provide a catalyst system in which efficiency drop of a catalyst formed by contacting a catalyst powder with a binder is avoided.

This object is achieved by a catalyst system for olefin metathesis, the catalyst system comprising: a) a first system zone substantially comprising a layered double hydroxide; and b) a second system zone comprising a metathesis catalyst.

DETAILED DESCRIPTION OF THE INVENTION

The catalyst system, in accordance with the present invention, when being mounted and ready for the intended use in olefin metathesis the first system zone is placed upstream with respect to the second system zone, preferably immediately upstream. Upstream means in this regard that a feed stream which is contacted with the catalyst system for converting compounds comprised in the feed stream will first be contacted with the first (upstream) system zone and is afterwards contacted with the second (downstream) system zone. In this regard, it is preferred that the catalyst is used in a catalyst bed.

The layered double hydroxide (LDH) comprised in the first system zone can be placed in a reactor separated from the metathesis catalyst reactor, that is, the first system zone and the second system zone are spatially separated. This arrangement is illustrated as alternative 1 in FIG. 1. It is also possible that the first system zone substantially comprising the LDH and the second system zone comprising the metathesis catalyst are placed in the same reactor in a layered structure, as it is illustrated as alternative 2 in FIG. 1.

Substantially comprising in terms of the present invention shall be understood as that the respective system zone does not contain any further (catalytic) active species (or only in amounts not significantly influencing the catalytic properties of the respective system zone and the catalyst system). That is, it is possible that the respective system zone substantially comprising the LDH (the first system zone) further comprises inert materials not having a (negative) impact on the behavior of the respective zone and the catalyst system. It may be preferred that the second system zone substantially comprises metathesis catalyst. In this regard, it is preferred that the first system zone consists of a layered double hydroxide. In the same way, it is preferred that the second system zone consists of a metathesis catalyst.

Preferably the metathesis catalyst comprised in the second system zone comprises a transition metal selected from Group VIA and VIIA of the Periodic Table of Elements supported on an inorganic support.

In context of the present invention, the term "Group VIA" is related to the Group 6 elements of the chromium group, i.e. Cr, Mo and W. In the same way, the term "Group VIIA" is related to the Group 7 elements of the manganese group, i.e. Mn, Tc and Re.

In preferred embodiments, parts by weight with respect to constituents of the inventive catalyst is percent by weight.

It is preferable that the transition metal used in this catalyst is selected from the group consisting of molybdenum, tungsten, and rhenium, which are highly active in metathesis reaction. The transition metal can be present in various Ruins including a metal element, oxide, sulfide, hydride, and hydroxide of the transition metal. In particular, oxides such as $WO_3$, $MoO_3$, and $Re_2O_7$ are preferable, and $WO_3$ is even more preferable. In an embodiment, the catalyst of the present invention comprises 1 to 15 parts by weight, preferably 7 to 11 parts by weight, of the transition metal.

A variety of inorganic supports is well known in the art. The types of the inorganic support are not particularly limited. In a preferred embodiment, the inorganic support is selected from the group consisting of silica, alumina, titania, zirconia, and mixtures thereof, preferably silica, alumina, and a mixture thereof.

In a preferred embodiment, the metathesis catalyst comprised in the second system zone further comprises 0.1 to 60 parts by weight of zeolite.

The types of zeolite are not limited, but can be preferably selected from the group consisting of ZSM-5, X-zeolite, Y-zeolite, beta-zeolite, MCM-22, ferrierite, or mixtures thereof. In a preferred embodiment, the zeolite is selected from the group consisting of ZSM-5, and Y-zeolite, or ferrierite, more preferably Y-zeolite.

Preferably, the content of zeolite in the metathesis catalyst is in the range of 0.5-30 parts by weight, more preferably 1-20 parts by weight.

In a further preferred embodiment, the metathesis catalyst comprised in the second system zone further comprises 0.1 to 80 parts by weight of a layered double hydroxide.

For the metathesis catalyst comprised in the second system zone, effect of the layered double hydroxide on the catalyst conversion, selectivity, and by product formation can be observed even at a low concentration. In an embodiment, the metathesis catalyst comprises 0.5-50 parts by weight, more preferably 1-30 parts by weight of the layered double hydroxide.

The first system zone comprises a layered double hydroxide (LDH). Also the metathesis catalyst comprised in the second system zone preferably comprises a LDH in preferred embodiments. Both of these LDHs are selected independently from each other, that is, the LDH comprised in the first system zone and the LDH of the metathesis catalyst comprised in the second system zone may or may not be the same. The description of preferred embodiments of LDH provided herein, in particular the detailed description provided below, are applicable for both of the LDH species.

The layered double hydroxides (LDH), also known as anionic clays or hydrotalcite-like materials, are a family of materials having a unique structure containing positively charged layers with charge-balancing anions and water interlayers. The general chemical formula of the layered double hydroxides can be written as:

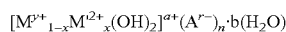

wherein
M is a first metal;
M' is a second metal;
A is an anion;
x is a number, preferably in the range of 0.1 to 0.9;
y is a charge number of the first metal, preferably equal to 1 or 2;
z is a charge number of the second metal, preferably equal to 3 or 4;
a is determined by x, y, and z, preferably a=(1−x)y+xz−2;
r is a charge number of the anion;
is determined by a and r, preferably n=a/r;
b is a number of water molecules, preferably in the range of 0-10.

The first metal (M) and the second metal (M') can be alkali, alkaline earth, transition, or other metals. In a preferred embodiment, the first metal is selected from the group consisting of Li, Ca, Mg, Mn, Fe, Co, Ni, Cu, Zn, and mixtures thereof, preferably Ca, Mg, Zn, and mixtures thereof. In another preferred embodiment, the second metal is selected from the group consisting of Al, Ga, In, Mn, Fe, Co, Cr, Ni, V, Ti, Zr, Y, and mixtures thereof, preferably Al.

Preferred examples of the anions include chloride, bromide, carbonate, bicarbonate, hydrogen phosphate, dihydrogen phosphate, nitrite, borate, nitrate, sulfate, phosphate, hydroxide, fluoride, iodide, and mixtures thereof. In a very preferred embodiment, the anion is selected from the group consisting of carbonate and/or nitrate.

Both synthetic and naturally occurring layered double hydroxide materials can be employed in the present invention.

In preferred embodiments, the metathesis catalyst further comprises a binder. Examples of suitable binders for the metathesis catalyst of this present invention include materials in the group of inorganic oxide, inorganic oxide sol, and clays.

Even more preferred, the weight ratio of the layered double hydroxide comprised in the first system zone and the metathesis catalyst comprised in the second system zone (layered double hydroxide to metathesis catalyst ratio) is from 0.5:1 to 10:1 by weight, preferably from 1:1 to 5:1, even preferred 2:1 to 4:1, most preferably about 3:1.

Preferably, the layered double hydroxide comprised in the first system zone and/or the layered double hydroxide of the metathesis catalyst comprises a first metal selected from the group consisting of Li, Ca, Mg, Mn, Fe, Co, Ni, Cu, Zn, and mixtures thereof, preferably Ca, Mg, Zn, and mixtures thereof.

It is preferred that the layered double hydroxide comprised in the first system zone and/or the layered double hydroxide of the metathesis catalyst comprises a second metal selected from the group consisting of Al, Ga, In, Mn, Fe, Co, Cr, Ni, V, Ti, Zr, Y, and mixtures thereof, preferably is Al.

Preferably, the layered double hydroxide comprised in the first system zone and/or the layered double hydroxide of the metathesis catalyst comprises an anion selected from the group consisting of chloride, bromide, carbonate, bicarbonate, hydrogen phosphate, dihydrogen phosphate, nitrite, borate, nitrate, sulfate, phosphate, hydroxide, fluoride, iodide, and mixtures thereof, preferably carbonate and/or nitrate.

The object of the present invention is further achieved by olefin metathesis process comprising contacting a feed stream, the feed stream comprising an olefin, with the inventive catalyst system.

Preferably, the feed stream comprises a linear olefin selected from the group consisting of C2 linear olefin, C3 linear olefin, C4 linear olefin, C5 linear olefin, C6 linear olefin, and mixtures thereof.

It is preferred that the process is conducted within a temperature range from 100 to 600° C., preferably 200 to 450° C.; and/or preferably at a pressure between 1 to 50 bar gauge.

Surprisingly, the inventors have found that by placing a bed of a layered double hydroxide (LDH) catalyst upstream to a metathesis catalyst, product selectivity, product yield, and stability of the reaction can be improved and the effect of binder and catalyst shaping process to the catalyst efficiency can be significantly avoided.

The catalyst system according to the present invention can be regenerated to remove buildups of poisonous substances, coke, carbon, and/or polymer on the catalyst surface after it has undergone a period of reaction to resume its activity. It is important to control condition of the regeneration step so that a satisfying level of buildups removal is achieved while pore structure, active sites, and other original catalytic functions are not excessively altered or destroyed. Conventionally known methods of heterogeneous catalyst regeneration can be used without limitation. Examples of regeneration process which can be used with the inventive catalyst system can be found in Applied Catalysis A: General 255 (2003) 133-142, U.S. Pat. App. Pub. No. 2010/0167911A1 and U.S. Pat. No. 4,522,936.

The invention works for the olefin metathesis reaction, most preferably in the olefin metathesis reaction between ethene and butene to produce propene. Additional features and advantages of the present invention will become apparent in the following detailed description on the basis of examples with reference to the drawings, wherein FIG. 1 illustrates two embodiments of the inventive catalyst system.

Figure 2:
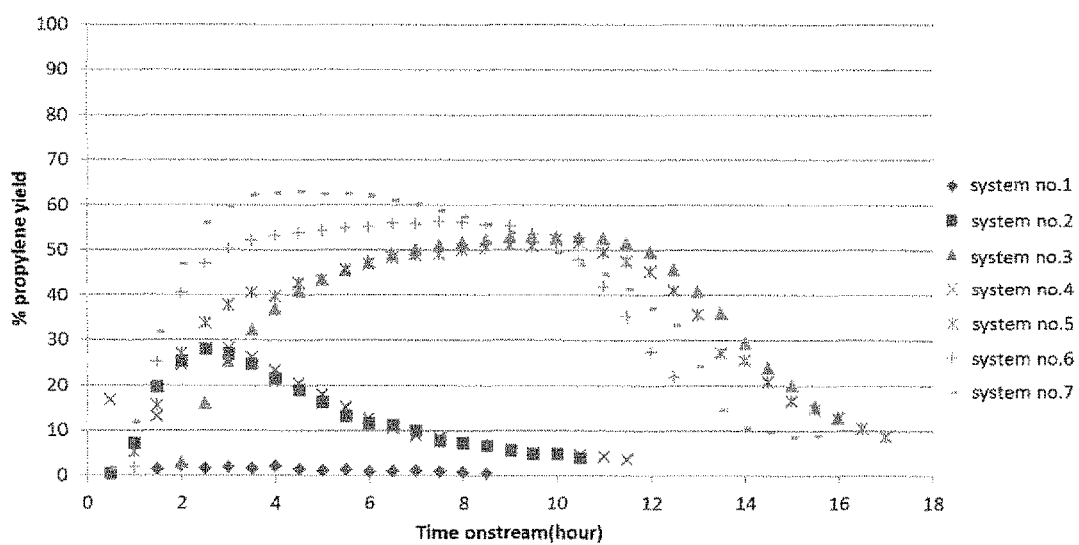

FIG. 2 illustrates propene yield results of various catalyst systems measured along reaction time on stream.

EXAMPLE 1 (COMPARATIVE)

Metathesis catalyst powder is obtained by depositing 9 wt % of $WO_3$ on a support containing 95 wt % of silica and 5 wt % of Y-zeolite and then physically mixing with Mg—Al—$CO_3$ layered double hydroxide in the ratio of 10:1 by weight. The catalyst powder was packed in a tube reactor, then a feed stream comprising ethene and 2-butene was supplied to react over the catalyst at 350° C. and 22 bar gauge to produce propene. Propene yield achieved was 61 wt %.

EXAMPLE 2

A metathesis catalyst was obtained by physically mixing 9 wt % $WO_3$ on a support containing 95 wt % of silica and 5 wt % of Y-zeolite with Mg—Al—$CO_3$ layered double hydroxide in the ratio of 10:1 by weight. 2.2 g of white clay (binder) and 110 mL of demineralized water was added to 110 g of the metathesis catalyst and the powder and water are immediately threshed to activate the binder and get homogeneous wet pre-extruded catalyst. Next, the wet catalyst is fed into an extruder. Then, the catalyst extrudate, getting from the extruder, is dried at 150° C. for 3-4 hr in an oven. The obtained catalyst was subjected to a reaction test where ethene and 2-butene are reacted to form propene over the catalyst at 350° C. and 22 bar gauge with 3 options of the upstream system zone as follow for comparison.

TABLE 1

| Upstream system zone | Propene yield (wt %) |
|---|---|
| None | 35 |
| MgO | 70 |
| Mg—Al—CO3 LDH | 99 |

It can be seen from the above results that placing a bed of a layered double hydroxide catalyst upstream to a metathesis catalyst can relieve, and even improve, catalyst efficiency drop occurred after catalyst shaping.

EXAMPLE 3

Various catalyst systems were prepared as displayed in Table 2.

TABLE 2

| Catalyst System No. | First system zone (upstream) | Second system zone (downstream) |
|---|---|---|
| 1 | — | 10 wt % $WO_3$/90 wt % $Si_2O_3$ |
| 2 | MgO | 10 wt % $WO_3$/90 wt % $Si_2O_3$ |
| 3 | Mg—Al—$CO_3$ LDH | 10 wt % $WO_3$/90 wt % $Si_2O_3$ |
| 4 | MgO | 10 wt % $WO_3$/78 wt % $Si_2O_3$/3 wt % Y-zeolite/9 wt % Mg—Al—CO3 LDH |
| 5 | Mg—Al—$CO_3$ LDH | 10 wt % $WO_3$/78 wt % $Si_2O_3$/3 wt % Y-zeolite/9 wt % Mg—Al—CO3 LDH |
| 6 | Mg—Al—$NO_3$ LDH | 10 wt % $WO_3$/78 wt % $Si_2O_3$/3 wt % Y-zeolite/9 wt % Mg—Al—CO3 LDH |
| 7 | Zn—Al—$CO_3$ LDH | 10 wt % $WO_3$/78 wt % $Si_2O_3$/3 wt % Y-zeolite/9 wt % Mg—Al—CO3 LDH |

These catalyst systems were subjected to reaction test by packing 1.5 grams of the second system zone (downstream) material as a bottom layer and 3 grams of the first system zone (upstream) material as a top layer in a tube reactor. A feed stream containing approximately 25 wt % ethene, 15 wt % n-butenes, 5 wt % i-butene, and balancing C4 paraffins were fed into the reactor to contact with the catalyst system at 350° C., 20 bar gauge, and WHSV 3.5 $h^{-1}$. Test results are displayed in Table 3.

TABLE 3

| Catalyst System No. | Total Butenes Conversion (wt %) | Selectivity to Propene (wt %) |
|---|---|---|
| 1 | 5 | 50 |
| 2 | 30 | 92 |
| 3 | 55 | 96 |
| 4 | 31 | 90 |
| 5 | 54 | 95 |
| 6 | 58 | 97 |
| 7 | 54 | 96 |

Propene yields measured along reaction time on stream are shown in FIG. 2.

It can be seen that activity, selectivity, and reaction stability were significantly improved when a bed of layered double hydroxide is placed upstream to the metathesis catalyst.

The features disclosed in the foregoing description and the figures and the accompanying claims may, both separately or in any combination, be material for realizing the invention in diverse forms thereof.

The invention claimed is:

1. An olefin metathesis process comprising contacting a feed stream comprising an olefin, with a catalyst system comprising:
   a. a first system zone comprising a first system zone layered double hydroxide (LDH); and
   b. a second system zone comprising a metathesis catalyst,
   wherein said first system zone LDH comprises a first LDH metal and a different, second LDH metal, said first LDH metal selected from the group consisting of Li, Ca, Mg, Mn, Fe, Co, Ni, Cu, and Zn and said second LDH metal selected from the group consisting of Al, Ga, In, Mn, Fe, Co, Cr, Ni, V, Ti, Zr, Y;
   wherein the metathesis catalyst comprises a transition metal selected from the group consisting of Cr, Mo, W, Mn, Tc, and Re, said transition metal being supported on an inorganic support;
   wherein the first system zone and the second system zone have different compositions; and
   wherein the contacting of the feed stream with the catalyst system is performed with temperatures in the first system zone and the second system zone from 200° C. to 450° C.

2. The process of claim 1, wherein the first system zone is placed upstream with respect to the second system zone.

3. The process of claim 1, wherein the metathesis catalyst comprises 0.1 to 60 parts by weight of a zeolite.

4. The process of claim 3, wherein the metathesis catalyst comprises 1 to 20 parts by weight of the zeolite.

5. The process of claim 1, wherein the metathesis catalyst comprises 0.1 to 80 parts by weight of a second system zone layered double hydroxide.

6. The process of claim 5, wherein the metathesis catalyst comprises 1 to 30 parts by weight of the second system zone layered double hydroxide.

7. The process of claim 1, wherein the metathesis catalyst comprises a binder.

8. The process of claim 1, wherein a weight ratio of the first system zone layered double hydroxide to the metathesis catalyst is from 0.5:1 to 10:1 by weight.

9. The process of claim 8, wherein the weight ratio of the first system zone layered double hydroxide to the metathesis catalyst is from 2:1 to 4:1 by weight.

10. The process of claim 1, wherein the transition metal of the metathesis catalyst is selected from the group consisting of molybdenum, tungsten, rhenium, and mixtures thereof.

11. The process of claim 1, wherein the inorganic support of the metathesis catalyst is selected from the group consisting of silica, alumina, titania, zirconia, and mixtures thereof.

12. The process of claim 3, wherein the zeolite of the metathesis catalyst is selected from the group consisting of ZSM-5, X-zeolite, Y-zeolite, β-zeolite, MCM-22, ferrierite, and mixtures thereof.

13. The process of claim 1, wherein the first LDH metal is selected from the group consisting of Li, Ca, Mg, Fe, Co, Ni, Cu, Zn, and mixtures thereof.

14. The process of claim 13, wherein the second LDH metal is selected from the group consisting of Al, Ga, In, Fe, Co, Cr, Ni, V, Ti, Zr, Y, and mixtures thereof.

15. The process of claim 1, wherein the first system zone layered double hydroxide comprises an anion selected from the group consisting of chloride, bromide, carbonate, bicarbonate, hydrogen phosphate, dihydrogen phosphate, nitrite, borate, nitrate, sulfate, phosphate, hydroxide, fluoride, iodide, and mixtures thereof.

16. The process of claim 1, wherein the feed stream comprises ethylene, propylene, or a linear olefin selected from the group consisting of a C4 linear olefin, a C5 linear olefin, a C6 linear olefin, and mixtures thereof.

17. The process of claim 1, wherein the metathesis catalyst comprises a second system zone layered double hydroxide comprising a second system zone first LDH metal selected from the group consisting of Li, Ca, Mg, Mn, Fe, Co, Ni, Cu, Zn, and mixtures thereof.

18. The process of claim 17, wherein the second system zone layered double hydroxide further comprises a second system zone second LDH metal selected from the group consisting of Al, Ga, In, Mn, Fe, Co, Cr, Ni, V, Ti, Zr, Y, and mixtures thereof.

19. The process of claim 1, wherein the metathesis catalyst comprises a second system zone layered double hydroxide comprising an anion selected from the group consisting of chloride, bromide, carbonate, bicarbonate, hydrogen phosphate, dihydrogen phosphate, nitrite, borate, nitrate, sulfate, phosphate, hydroxide, fluoride, iodide, and mixtures thereof.

20. The process of claim 1, wherein the first system zone does not comprise any further catalytic active species, or comprises said further catalytic active species only in an amount that does not significantly influence catalytic properties of the first system zone.

* * * * *